United States Patent [19]
Bogue et al.

[11] Patent Number: 5,662,849
[45] Date of Patent: Sep. 2, 1997

[54] METHOD AND APPARATUS FOR FORMING COMPRESSION DOSAGE UNITS WITHIN THE PRODUCT PACKAGE

[75] Inventors: Beuford Arlie Bogue, Broad Run; Garry L. Myers, Reston, both of Va.

[73] Assignee: Fulsz Technologies Ltd., Chantilly, Va.

[21] Appl. No.: 438,239

[22] Filed: May 9, 1995

Related U.S. Application Data

[63] Continuation-in-part of Ser. No. 276,244, Jul. 18, 1994, which is a continuation-in-part of Ser. No. 259,496, Jun. 14, 1994, abandoned, and Ser. No. 259,258, Jun. 14, 1994, which is a continuation-in-part of Ser. No. 133,669, Oct. 7, 1993, Pat. No. 5,597,416, and Ser. No. 119,974, Sep. 10, 1993, Pat. No. 5,518,551.

[51] Int. Cl.$^6$ ............................................. B29C 43/08
[52] U.S. Cl. .................. 264/112; 264/109; 264/123; 425/347; 425/348 R; 425/350
[58] Field of Search ...................... 264/109, 112, 264/120, 123; 425/347, 348 R, 350

[56] References Cited

U.S. PATENT DOCUMENTS

| | | | |
|---|---|---|---|
| 2,068,619 | 1/1937 | Bailey | 425/353 |
| 2,214,505 | 9/1940 | Magnenat | 18/16 |
| 3,175,521 | 3/1965 | Hershberg | 425/347 |
| 3,616,493 | 11/1971 | Okubo et al. | 425/347 |
| 4,376,111 | 3/1983 | Tovey | 424/15 |
| 4,493,822 | 1/1985 | Tovey | 424/15 |
| 4,880,373 | 11/1989 | Balog et al. | 425/149 |
| 4,943,227 | 7/1990 | Facchini | 425/345 |
| 5,087,398 | 2/1992 | Le Molaire et al. | 264/112 |

Primary Examiner—Mary Lynn Theisen
Attorney, Agent, or Firm—Hoffmann & Baron

[57] ABSTRACT

The present invention provides a method and apparatus for forming a compression dosage unit such as a tablet. The method of the present invention includes dispensing a premeasured volume of tableting feedstock into a product tray. The feedstock is compacted into a tablet within the product tray. The product tray may be further packaged for distribution and sale. The apparatus of the present invention includes a dossiter for dispensing the premeasured volume of feedstock into the product tray from a reservoir. A die is insertable into the product tray to form the tablet therein. The present invention also provides for the formation of the tablets within the product tray by use of the dossiter.

31 Claims, 8 Drawing Sheets

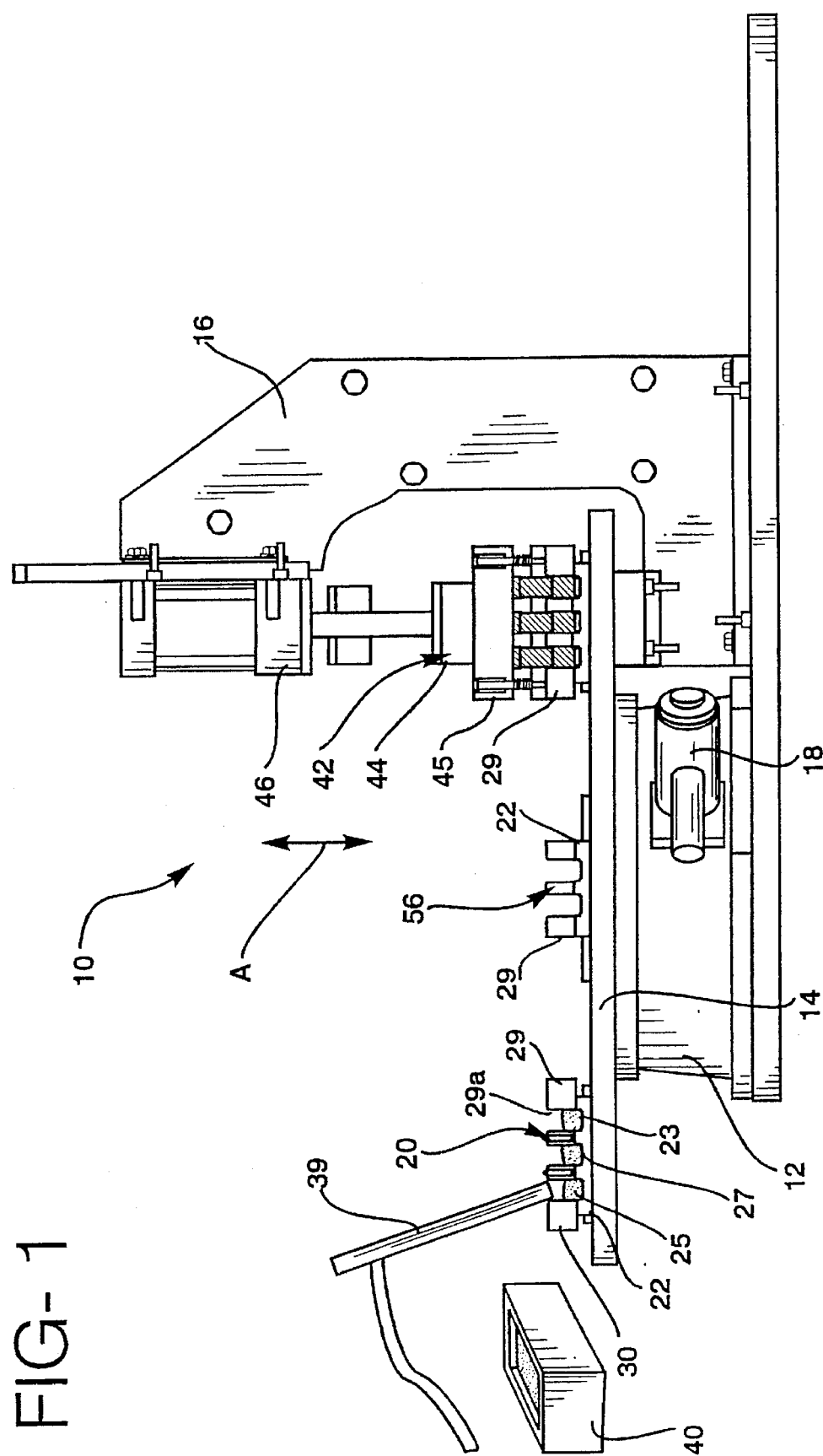

1

METHOD AND APPARATUS FOR FORMING COMPRESSION DOSAGE UNITS WITHIN THE PRODUCT PACKAGE

CROSS REFERENCE TO RELATED APPLICATIONS

The present application is a continuation-in-part of U.S. application Ser. No. 08/276,244 filed Jul. 18, 1994 (Attorney's Docket No. 447-103) which is a continuation-in-part of U.S. application Ser. No. 08/259,496 filed Jun. 14, 1994 (Attorney's Docket No. 447-105) now abandoned, and U.S. application Ser. No. 08/259,258 filed Jun. 14, 1994 (Attorney's Docket No. 447-106), which is a continuation-in-part of U.S. application Ser. No. 08/133,669 filed Oct. 7, 1993 (Attorney's Docket No. 447-66) now U.S. Pat. No. 5,597,416 and U.S. application Ser. No. 08/119,974 filed Sep. 10, 1993 (Attorney's Docket No. 447-85) now U.S. Pat. No. 5,518,551. The contents of each of these copending, commonly-owned applications is incorporated herein by reference.

FIELD OF THE INVENTION

The present invention relates generally to a method and apparatus for forming compression dosage units, more specifically tablets. The present invention more particularly relates to forming tablets, preferably low density tablets, from tableting feedstock within the tablet package.

BACKGROUND OF THE INVENTION

Dosage units in the form of tablets are prepared by compressing a formulation containing a medicinal substance or drug and other ingredients, such as excipients selected for properties which enhance the production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

Other methods of preparing feedstock for preparing compression dosage units have been disclosed in the above-referenced copending applications as well as in copending, commonly owned U.S. application Ser. No. 08/194,682 filed Feb. 10, 1994. Each of these applications are incorporated herein by reference.

U.S. application Ser. No. 08/194,682 discloses a method of making a solid comestible by compressing shearform matrix masses sufficiently to form a comestible compression unit. U.S. application Ser. No. 08/259,496 discloses a method of preparing a quick dissolve comestible unit by mixing uncured shearform matrix and an additive, molding a unit dosage form therefrom, and curing the shearform matrix. Finally, U.S. application Ser. No. 08/259,258 discloses a method of preparing quick dissolve comestible units by initiating crystallization of shearform matrix, and combining, either before or after initiating crystallization, an additive with the shearform matrix to form flowable, compactible micro-particulates. Finally, the micro-particulate medium is compacted to form the quick dissolve comestible unit. In each of these disclosures, the tableting medium is prepared initially by use of shearform matrix. In most cases a quick dissolve tablet can be produced by providing a compressed body which is of low density and capable of being disintegrated and dispersed relatively rapidly, and in many cases, instantaneously.

Tableting processes known today in the art generally include the use of a machine which includes opposing punches and cavities into which a tableting medium can be directed and subjected to compression between the punches. See, for example, U.S. Pat. No. 4,943,227; U.S. Pat. No. 4,880,373; U.S. Pat. No. 2,214,505 and U.S. Pat. No. 2,068,619. Other references which disclose different shapes of dosage units are U.S. Pat. No. 4,493,822, U.S. Pat. No. 4,376,111, and an excerpt from The Consumer Guide for "Prescription Drugs," p. 194–208, Publications International, Ltd. (1990).

In the manufacturing of low density tablets, a newly formed tablet is relatively fragile and must go through a curing process over time where the tablet hardens so that it can be easily handled, packaged and distributed. Quite often attempts to package a newly formed tablet result in damage to the tablet itself. This necessitates waiting a period of time before packaging the tablet or taking extra precautionary steps in the handling of the tablet during the packaging phase. Each of these solutions obviously increases the difficulty and cost involved in forming and packaging tablets.

It is therefore desirable to provide a method and apparatus for enabling the formation of tablets directly in the product package. This will enable the tablet to be formed and packaged without handling delay or extra processing steps.

SUMMARY AND OBJECTS OF THE INVENTION

It is an object of the present invention to provide a method and apparatus for forming a compression dosage unit directly in the package for the dosage unit. The method provides for the formation of a tablet within a tablet package which permits the distribution and sale of the tablets in the package. The process of the present invention includes providing a tablet package having an open ended cavity generally in the shape of the desired tablet. A premeasured volume of tableting feedstock material is deposited within the cavity. The tableting feedstock material is compacted within the open ended cavity so as to form the desired tablet. The package may then be sealed for ultimate distribution and sale.

In its apparatus aspect, the present invention provides an apparatus for the production of tablets within a tablet package. The apparatus includes a first station which accommodates a tablet package having an open ended cavity generally in the shape of the tablet. At a second station, a premeasured volume of tableting feedstock is dispensed into the open ended cavity of the tablet package. At a third station, the premeasured volume of tableting feedstock within the cavity is compacted into the tablet shape. It is further contemplated that the apparatus may include additional stations which fully enclose the tablet within the tablet package for subsequent distribution and sale.

As more particularly described by way of the preferred embodiments herein, the present invention includes a supporting table which supports the tablet package. The supporting table includes a portion having configuration generally matching the tablet package to support the package therein. During the compacting of the premeasured volume of tableting feedstock, the table portion supports the tablet package during the formation of the tablet.

BRIEF DESCRIPTION OF THE DRAWINGS

FIG. 1 is a side elevational showing of an apparatus used to form a compression dosage unit, such as a tablet, within a tablet package.

DETAILED DESCRIPTION OF THE PREFERRED EMBODIMENT

Figure 2B:
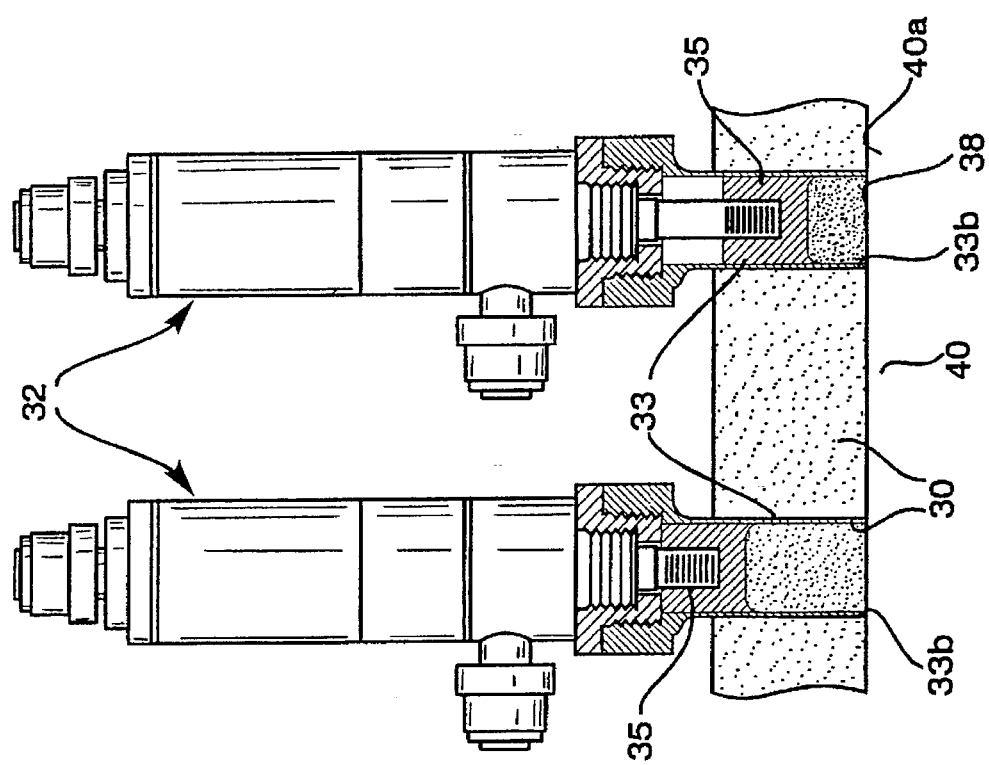
FIGS. 2A through 2D shows a dossiter of the present invention and the successive steps employed to compact tableting feedstock in the tablet package with the dossiter.

The present invention is a unique method and apparatus for preparing compression dosage units, such as tablets, and for forming the units in the tablet package. The term "tablet" is used herein to mean a unit having two sides, sometimes referred to as a top and a bottom, and a continuous edge which joins the top and the bottom. The entire mass of the material throughout the tablet is the "volume" of the tablet.

The mass of the units prepared in accordance with the present invention is continuous in the sense that the feedstock material used to prepare the units (tableting feedstock) is prepared in a single compression chamber, which may be defined by the tablet package and the face of the compressor, sometimes referred to as a "punch", but which may have two different densities. A first volume is associated with the edge in that it circumscribes the unit and includes the edge surface. A second volume, which is referred to as the "non-edge" portion, is within the edge portion. In the present illustrative example the feedstock is compressed and formed directly in a tablet package.

The method and apparatus of this invention are especially useful in making low density tablets and preferably tablets which undergo further curing or processing to form a rigid structure. The term low density is used herein to denote tablets wherein at least 60% and preferably 80% of the volume of the tablet has a density of less than 1.2 grams per cubic centimeter and preferably less than 0.8 grams per cubic centimeter. For preferred embodiments, the apparatus and process of the present invention are used to make high porosity tablets which have a porosity of 0.35 to 0.75 and preferably 0.45 to 0.65. Porosity as used herein is defines as: 1-(bulk density÷actual density).

In a preferred embodiment the non-edge portion of units prepared in accordance with the invention has a lower density, mass per unit volume, than the edge portion. The non-edge volume density is less than about 1.2 grams per cubic centimeter, preferably less than 0.8 grams per cubic centimeter, and most preferably not greater than 0.6 grams per cubic centimeter.

The edge portion of tablets prepared according to the invention have a higher density than the non-edge portion. The edge portion has a density which is at least about 10% greater than the density of the non-edge portion, preferably about 15% greater, and most preferably about 20% greater. Thus, if the density of the non-edge portion is about 0.6 grams per cubic centimeter, the density of the edge portion is preferably about 0.66 grams per cubic centimeter, preferably about 0.69 grams per cubic centimeter, and most preferably about 0.72 grams per cubic centimeter.

The extent of the edge portion is that amount of volume and surface sufficient to increase the "strength" of the unit for handling by processing machinery and personnel without deterioration of the unit. "Strength" includes both resistance to unit fracture and surface crumbling, i.e., friability.

A tableting feedstock material which is particularly useful in the present invention is saccharide based. Particularly useful feedstocks for the tableting process of this invention are disclosed in U.S. application Ser. No. 08/259,496 (Attorney Docket No. 447-105) and U.S. application Ser. No. 08/259,258 (Attorney Docket No. 447-106).

In another embodiment, the feedstock disclosed in U.S. application Ser. No. 08/194,682 filed Feb. 10, 1994 (Attorney Docket No. 447-80), which includes a free form agglomerate wherein selected ingredients such as a medicinal substance, and a carrier are fused together, is used in the process of the present invention. The free form agglomerate is distinguished from agglomerates formed from wet and dry granulations. The components of the tablet are thoroughly dispersed throughout the product because the mixture attained in the free form agglomerate is microstructurally stabilized against migration out of mixture. Fusion of the ingredients in a micro-structurally-stabilized mixture is achieved prior to compression as a result of flash flow processing. The feedstock includes a saccharide-based material which acts as a carrier for the medicament.

Preferred materials useful as matrices may be chosen from such classes as sugars or sugar derivatives. The term sugar is meant to include those carbohydrates having a high glucose profile. A high glucose profile means that the carbohydrate has a large number of six-carbon mono and disaccharides as well as other glucose-based oligomers. Mono-, di-, tri- and polysaccharides and their derivatives may be employed. Examples include glucose, sucrose, maltose, lactose, arabinose, xylose, ribose, fructose, mannose, pentoss, galactose sorbose, dextrose, sorbitol, xylitol, mannitol, pentatol, maltitol, isomalt, sucralose and mixtures thereof.

The carrier material can be selected from material which is capable of undergoing both physical and/or chemical changes associated with flash-flow processing. Materials useful as matrices may be chosen from those carbohydrates which are capable of forming free-form agglomerates upon being processed. Maltodextrins are an example of such carrier materials. Maltodextrins include those mixtures of carbohydrates resulting from hydrolysis of a saccharide feedstock which are described as solids having a DE of less than 45.

Polydextrose is also contemplated for use as a carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of copending U.S. application Ser. No. 07/881,612 filed May 12, 1992 (Attorney Docket No. 447-46) now abandoned.

The feedstock can also include maltooligo-saccharide produced by selective hydrolysis of cornstarch followed by removal of high and low molecular weight compounds. The general description of malto-oligosaccharides as contemplated herein is set forth in above-identified U.S. application Ser. No. 07/847,595 now abandoned.

Referring to the drawings the method and apparatus for forming tablets in a tablet package in accordance with the present invention may be described.

Referring now to FIG. 1, a tableting apparatus 10 which may be used in accordance with the present invention is shown. Tableting apparatus 10 includes a base 12, a rotatably movable table 14 supported by base 12 and an overhead arm 16 also supported by base 12. A drive motor 18 positioned beneath rotatable table 14 provides for the controlled rotational movement thereof.

As shown in FIG. 1, a first station 20 is provided on table 14. First station 20 defines a fill station which includes a support member 22 positioned on table 14. Support member 22 includes a plurality of individual chambers 23. Support member 22 is an upwardly opening block which provides for the support of a product tray 25 shown more particularly in FIGS. 5 and 6. Product tray 25 is generally a rectangular member preferably formed of transparent or translucent plastic, aluminum foil or an aluminum/plastic laminate having a plurality of cavities 27 which are generally in the shape of the tablet which is formed by the apparatus of the present invention. Each cavity 27 is positionable in one of the chambers 23 of support member 22. In this regard support member 22 includes chambers 23 arranged in a pattern which matches the pattern of cavities 27 of product tray 25. This positionally confines tray 25 on movable table 14 and provides structural integrity for further processing in accordance with the present invention. Product tray 25 is of the type known in the industry as a blister pack and may be used in combination with a covering such as a layer of metallic foil and/or plastic which suitably closes the blister pack containing the tablets and prevents deterioration of the tablet by force and/or environmental conditions. The product tray 25 becomes the package in which the tablets are shipped, sold and dispensed. The present invention provides a technique for forming tablets directly into the product package; thereby eliminating the need for additional packaging steps during tablet formation. This reduces the cost and complexity of tablet manufacture.

As shown, support member 22 further supports a filling block 29 which is positionable over product tray 25 which is seated within support member 22. Filling block 29 includes a plurality of elongate upwardly opening channels 29a each disposed over an individual cavity 27 of tray 25. Filling block 29 defines a containment area together with cavities 27 which accommodate a premeasured volume of tableting feedstock 30 dispensed thereinto. As will be described hereinbelow, channels 29a of filling block 29 permit the accommodation of dies used to form the tablets in cavities 27.

Referring still to first station 20 of tableting apparatus 10, tableting feedstock 30 of the type which is described above may be deposited within cavities 27 of product tray 25 supported by support member 22. Tableting feedstock 30 may be deposited employing a variety of well known devices generally referred to as dossiters. One such dossiter is a simple wand-type dossiter 39 which may be used to deposit a premeasured volume of tableting feedstock 30 into each individual cavity 27 of product tray 25. Dossiter 39 is repetitively inserted into a reservoir 40 to collect a premeasured volume of tableting feedstock 30. The dossiter is then moved to the tray 25 at first station 20 to deposit the premeasured volume of tableting material 30 into the individual cavities 27. Other structures and arrangements of dossiters may also be employed where the cavities 27 of product tray 25 are filled in unison, for example, in a manner such as that described in further detail hereinbelow. It is contemplated that dossiter manipulation may be accomplished manually or may be automatically operated in conjunction with automated machinery.

In the embodiment shown in FIG. 1, dossiter 39 is employed to collect and deposit feedstock 30 into cavities 27. Thereafter other components of tableting apparatus 10, such as dies, are used to form the tablets. However, it is within the contemplation of the present invention to employ a dossiter to both collect the feedstock and form the tablet directly in the product package. One such dossiter 32 is shown in FIGS. 2A through 2D and is also shown and described in co-pending commonly assigned U.S. Patent application Ser. No. 08/437,300, now U.S. Pat. No. 5,653, 926, bearing Attorney's Docket Number 447-125 filed at an even date herewith which is incorporated by reference herein.

Figure 2A:
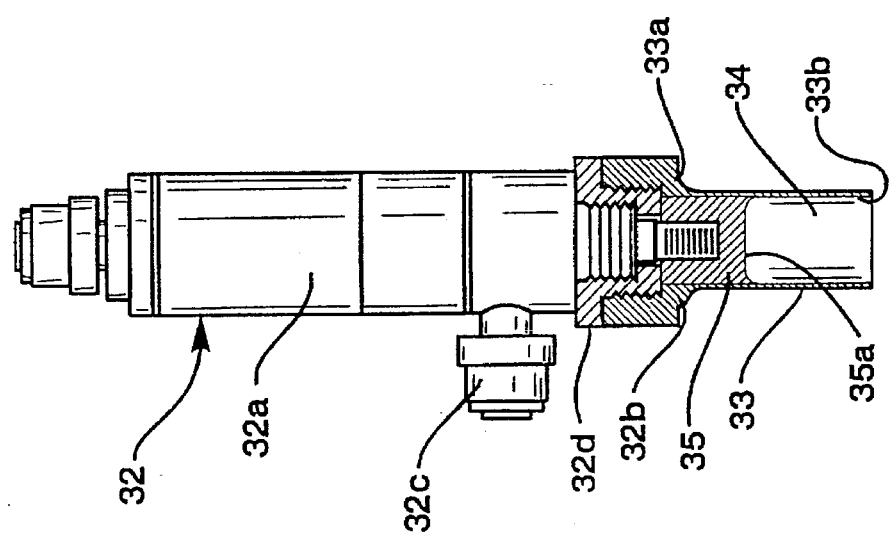

Referring now to FIG. 2A, a dossiter 32 of the present invention is shown. Dossiter 32 is a elongate member including an upper portion 32a and an opposed lower portion 32b. Upper portion 32a houses therein an operable mechanism (not shown) used to actuate dossiter 32 in accordance with the description set forth hereinbelow. Upper portion 32a may also include a connection device 32c which permits connection of an electrical or pneumatic control and power source to dossiter 32. Lower portion 32b of dossiter 32 includes a mechanical coupling 32d which effects attachment of lower portion 32b to upper portion 32a.

Lower portion 32b, defines an accumulation chamber or die 33. Accumulation chamber 33 is generally an elongate hollow cylindrical member having a closed first end 33a attached to coupling 32d and an opposed open end 33b defining a cylindrical die cavity 34 therebetween. Movably supported within die cavity 34 is an actuatable piston-like die punch 35 which is movable within die cavity 34 toward and away from open end 33b. Die punch 35 is operable under the power mechanism connected to connection device 32c of dossiter 32 for controlled movement within die cavity 34. Die punch 35 includes a tablet forming surface 35a facing open end 33b of chamber 33. The construction and shape of tablet forming surface 32 may be of the type more fully described in a commonly assigned U.S. patent application Ser. No. 08/438,165, now U.S. Pat. No. 5,648,033, bearing Attorney Docket Number 447-124 filed an even date herewith which is incorporated by reference herein.

Referring now to FIG. 2B, dossiter 10 is shown with accumulation chamber 33 inserted into a reservoir 40 containing tableting feedstock 30. Reservoir 40, as described above, is a constant level reservoir having a bottom surface 40a against which the open end 33b of accumulation chamber 33 is placed. Constant level reservoir 40 is designed to provide a consistent level of tableting feedstock 30 at all times within the reservoir 40. In this manner a constant predetermined volume of tableting feedstock will be accommodated within die cavity 34 of accumulation chamber 33 upon placement of the dossiter 32 into reservoir 40 with open end 33b being seated against the bottom surface 40a.

Initially dossiter 32 includes punch 35 located adjacent the open end 33b of chamber 33. Upon insertion into reservoir 40, the punch is forced upward toward closed end 33a. As the punch retracts, feedstock 30 fills the chamber 33 until the open end 33b engages the bottom surface 40a of reservoir 40.

As further shown in FIG. 2B, the predetermined volume of tableting feedstock 30 held within die cavity 33 may preferably be compressed into a tablet preform 38 by partial movement of die punch 35 in a direction back towards open end 33b of accumulation chamber 33. The predetermined volume of tableting feedstock 30 supported therein is slightly compressed into a low density tablet preform 38 against the bottom surface 40a of reservoir 40. The density of tablet preform 38 may be controlled by controlling the distance that die punch 35 moves within accumulation chamber 33. By compressing the tableting feedstock 36 into tablet preform 38, movement of the mass of tableting feedstock 30 by dossiter 32 is more easily facilitated as the preform 38 is easily retained in the chamber 33. Surface friction between the inner wall of chamber 33 and the slightly compressed preform, retains the preform 38 within chamber 33. However, even absent the formation of tablet preform 38, the tableting feedstock 36 contained within die cavity 34 may be moved, upon the movement of dossiter 10 without loss of the contents as the insertion of the open ended accumulation chamber into the filled reservoir establishes a vacuum holding the contents therein.

Figure 2D:
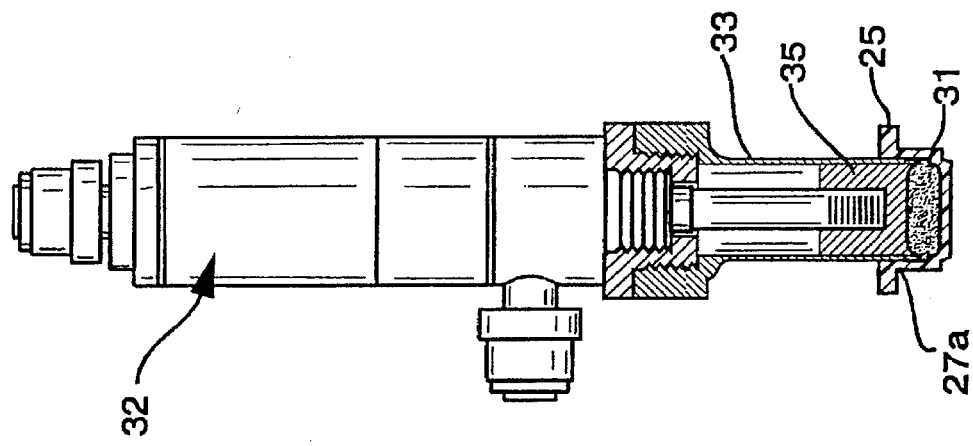
Figure 2C:
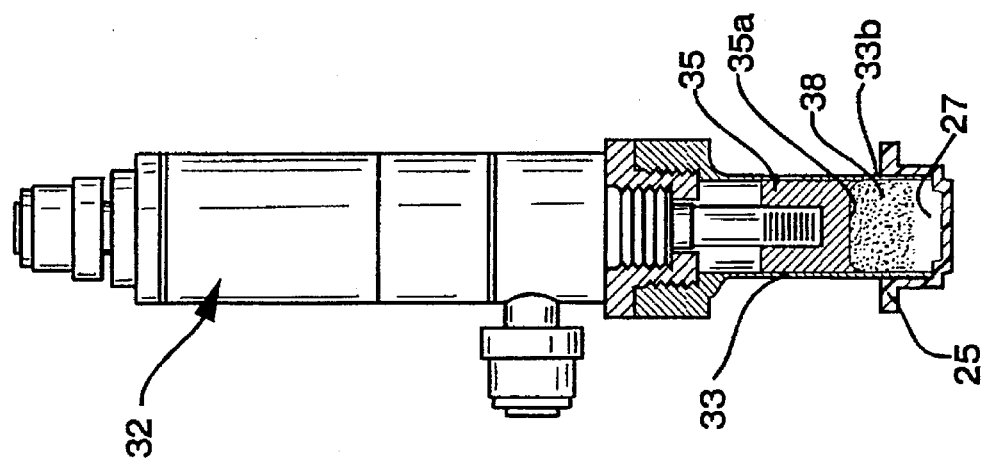

Referring now to FIGS. 2C and 2D, the use of dossiter 32 to form tablet 31 directly in a product tray 25 is shown. Upon accumulation of tableting feedstock 30 and the optional formation of tablet preform 38 within accumulation chamber 33, dossiter 32 is removed from reservoir 40 (FIG. 2B) and moved to a location where product tray 25 is positioned. Product tray 25 including cavity 27 is more fully shown in FIGS. 5 and 6, where cavities 27 of product tray 25 may have a cavity shape which is generally in the shape of the tablet 31 to be formed therein. Dossiter 32 is moved directly over one of the cavities 27 so that open end 33b of accumulation chamber 33 is positioned partially within cavity 27. Die punch 35 is movable within accumulation chamber 33 to compact the tablet preform 38 between the tablet forming surface 35a of die 35 and the package wall 27a about cavity 27. As shown in FIG. 2D, in the present illustrative embodiment, it is contemplated that the die punch 35 is moved within accumulation chamber 33 such that the tablet forming surface thereof extends slightly beyond open end 33b so as to permit the formation of the tablet 31 directly within cavity 27. Again by controlling the distance moved or force applied by die punch 35, a tablet 31 of specified density my be formed with accumulation chamber 20 directly in the cavity 27 of product tray 25. A product tray support (not shown) may be employed beneath product tray 25 to support and provide resistance for the compression of the feedstock in product tray 25 with punch 35.

In a preferred embodiment the dossiter 32 is used to collect the feedstock 30, form a tablet preform 38 and compress the preform 38 into a tablet 31 directly in the product tray 25. The dossiter 32 may also be used to transfer the tablet preform to a location where the preform 38 is compressed into tablets in the product tray 25 using separate tablet forming dies.

Returning now to the description of tableting apparatus 10 shown in FIG. 1, each cavity 27 is filled either with loose feedstock 30 using a simple wand-type dossiter 39, or with a tablet preform 38 using dossiter 32 shown in FIGS. 2A–2D. Support member 22 is moved on table 14 to a second station 42 which is adjacent arm 16. At second station 42 the premeasured volume of tableting feedstock 30 positioned within cavities 27 of product tray 25 and retained by filling block 29, are formed into tablets. This second station 42 includes a compression piston 44 movably supported over table 14 by arm 16. Such movable support may include a conventional reciprocating stoke mechanism 46 operable by an electromechanical mechanism (not shown) to provide for the vertical reciprocating movement thereof in the direction of arrow A.

Figure 3A:
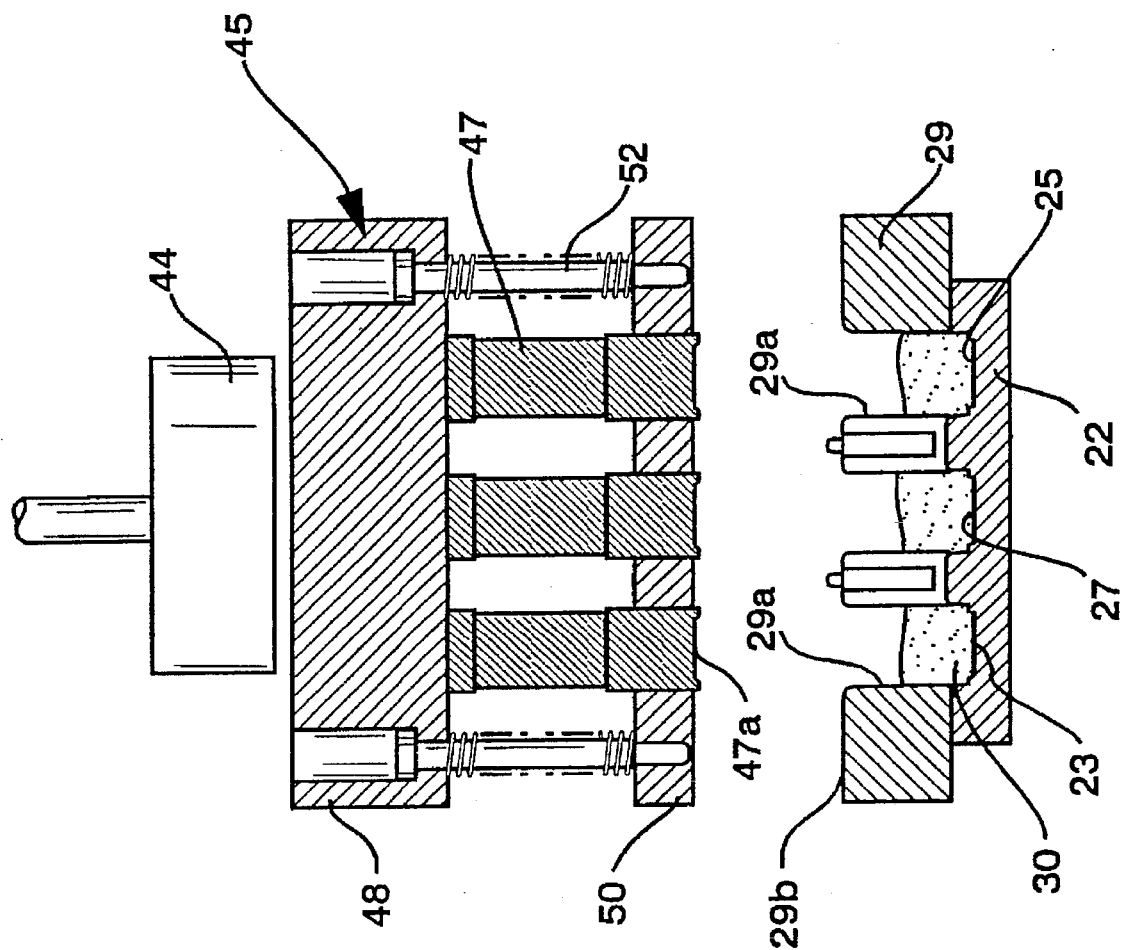
FIGS. 3A through 3C show the successive steps employed to compact the tableting feedstock in the tablet package using dies.
Figure 3B:
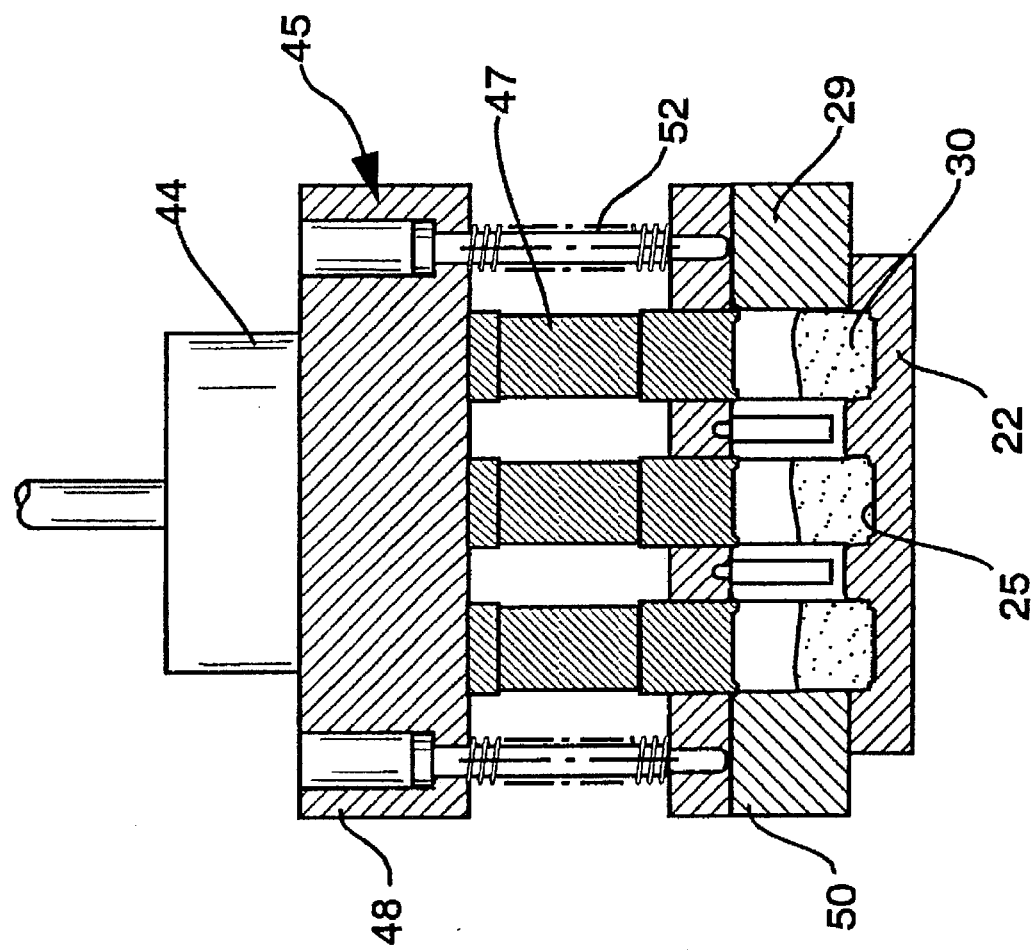
Figure 3C:
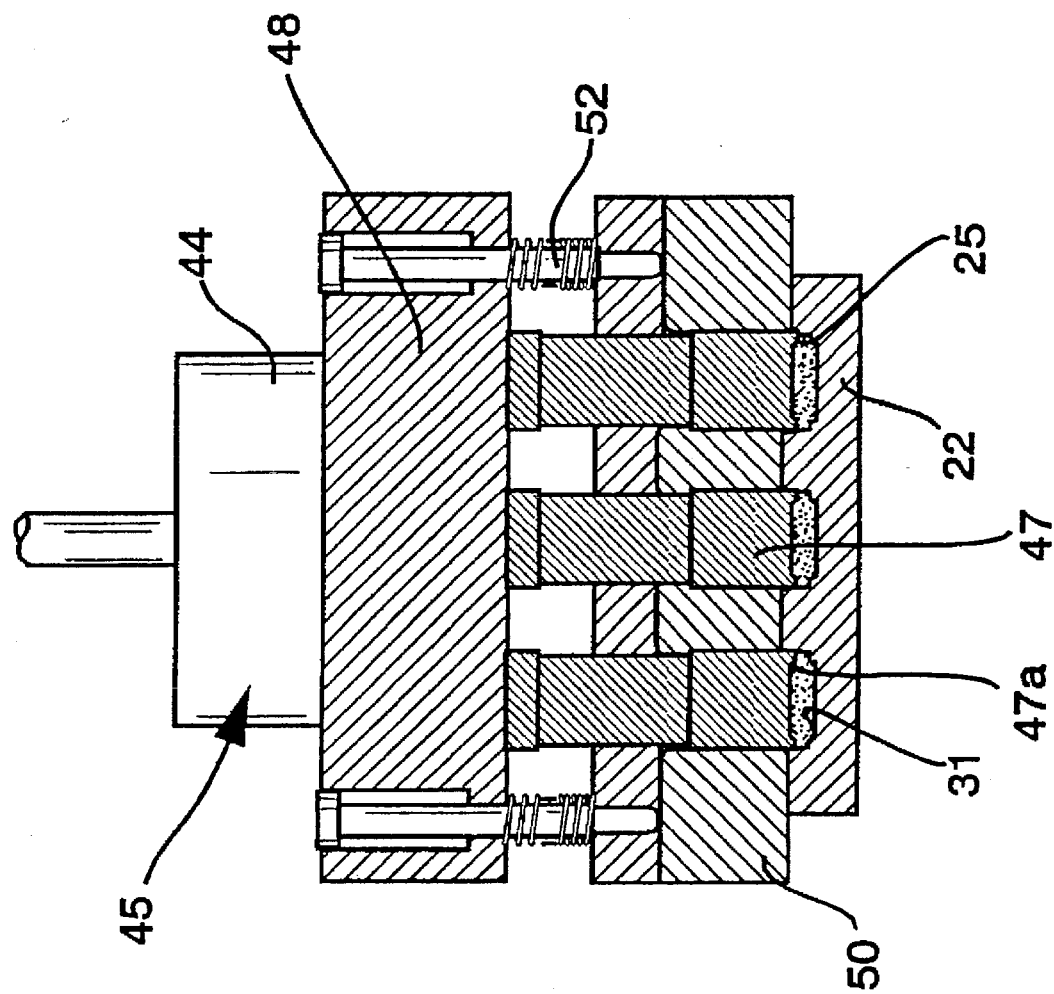

Second station 42 accommodates a die assembly 45 positioned over filling block 29. As shown in FIGS. 3A–3C, die assembly 45 includes a plurality of elongate rod-like punches or dies 47 each having a lower end 47a generally in the shape of the tablet to be formed. Dies 47 are supported by an upper support block 48 adjacent the upper ends of the dies and by a lower support block 50 adjacent the lower ends 47a. Blocks 48 and 50 are movable relative to one another under the bias of spring assembly 52. Dies 47 are constructed and arranged to be insertable into channels 29a of filling block 29 to facilitate the formation of tablets.

Referring more specifically to FIGS. 3A through 3C, the formation of tablets at second station 42 may now be described. Die assembly 45 is positioned over filling block 29. Lower support block 50 is supported against an upper surface 29b of filling block 29. Actuation of mechanism 46 (FIG. 1) causes downward movement of piston 44 into contact with upper support block 48 (FIG. 3B). Continued actuation of mechanism 46 causes downward movement of lower support block 50 against the bias of spring assembly 52. Such movement causes the individual dies 47 to be lowered in unison into chambers 29a of filling block 29 and over the tableting feedstock 30 contained therein. FIG. 3C shows die assembly 45 in the full-compacting stroke where the individual dies 47 are compressed against tableting feedstock 30 (or preform 38) to compress the feedstock and form tablets 31 between lower end 47a of die 47 and each cavity 27 of product tray 25.

From the position shown in FIG. 3C, after formation of tablets 31, piston 44 is retracted. Under the bias of spring assembly 52 upper support block 48 moves away from lower support block 50 moving dies 47 out from chambers 29a of filling block 29. Die assembly 45 is then removed. Each cavity 27 now supports a fully formed tablet 31 having a shape formed by lower ends 47a of die 47 and the cavity 27.

Referring again to FIG. 1, table 14 is again rotated so that support member 22 moves from its second station 42 to a third station 56 where the filling block 29 and filled product tray 25 may be removed and another empty product tray may be inserted into support member 22 to begin the cycle again. The three stations 20, 42 and 52 may be simultaneously operated in a continuous cyclical manner so that continuous production can be achieved.

The filled product tray 25 containing formed tablets 31 may now be further processed for ultimate distribution and sale.

As may be appreciated, the product tray 25 filled with formed tablets 31 permits the movement of the tablets without the need for individual handling. In prior tableting techniques, the newly formed tablets must be removed from the formation apparatus and inserted into package trays. This handling, especially immediately after formation, may cause the brittle tablet to break. By forming tablet 31 directly in the product package tray 25, the direct handling of the newly formed tablets and resulting brittle breakage is eliminated. Also eliminated is the additional step of tablet transfer which is necessitated in more conventional tablet forming apparatus.

Figure 4:
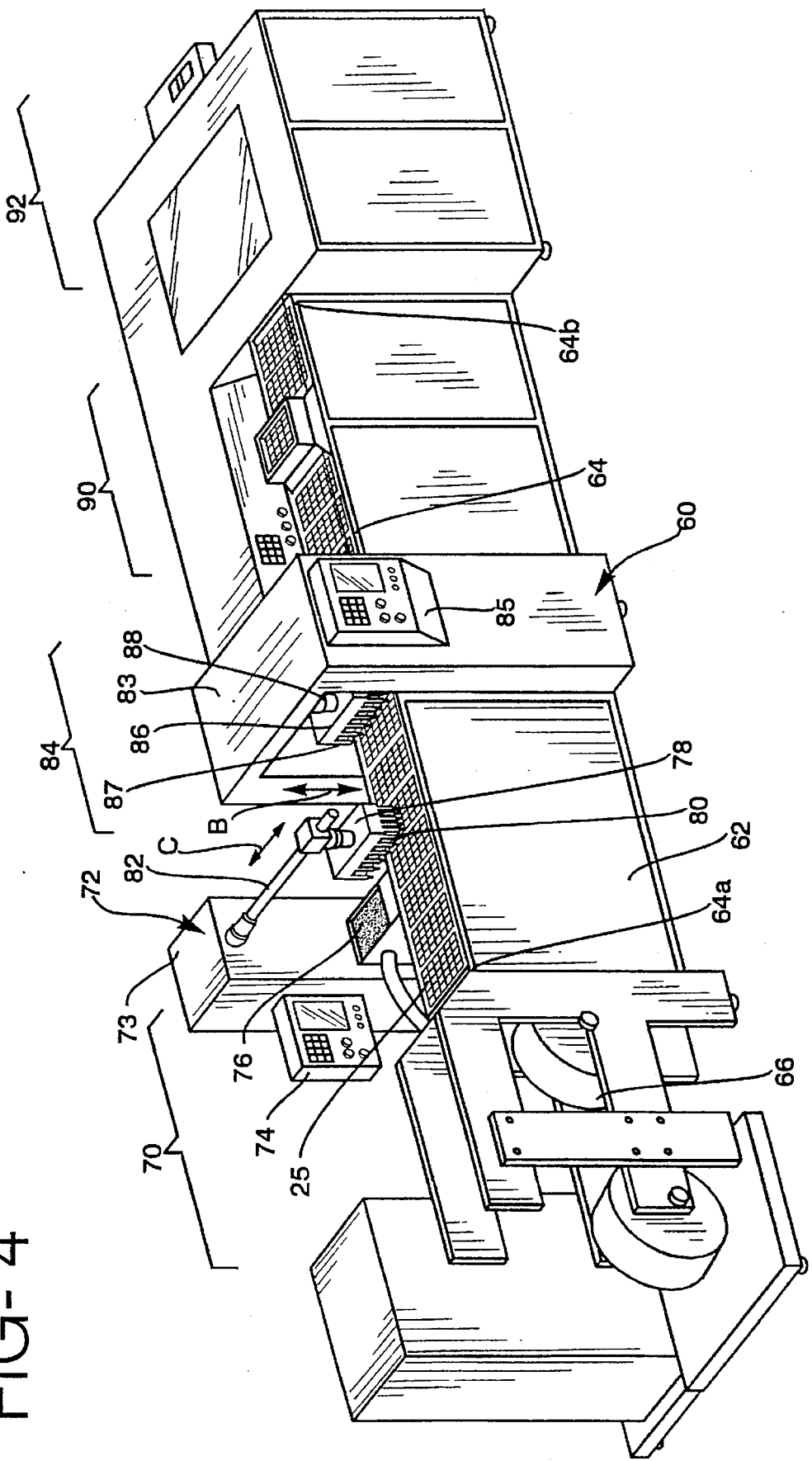
FIG. 4 shows a form, fill and seal apparatus of the present invention used to form tablets in a tablet package.
Figure 5:
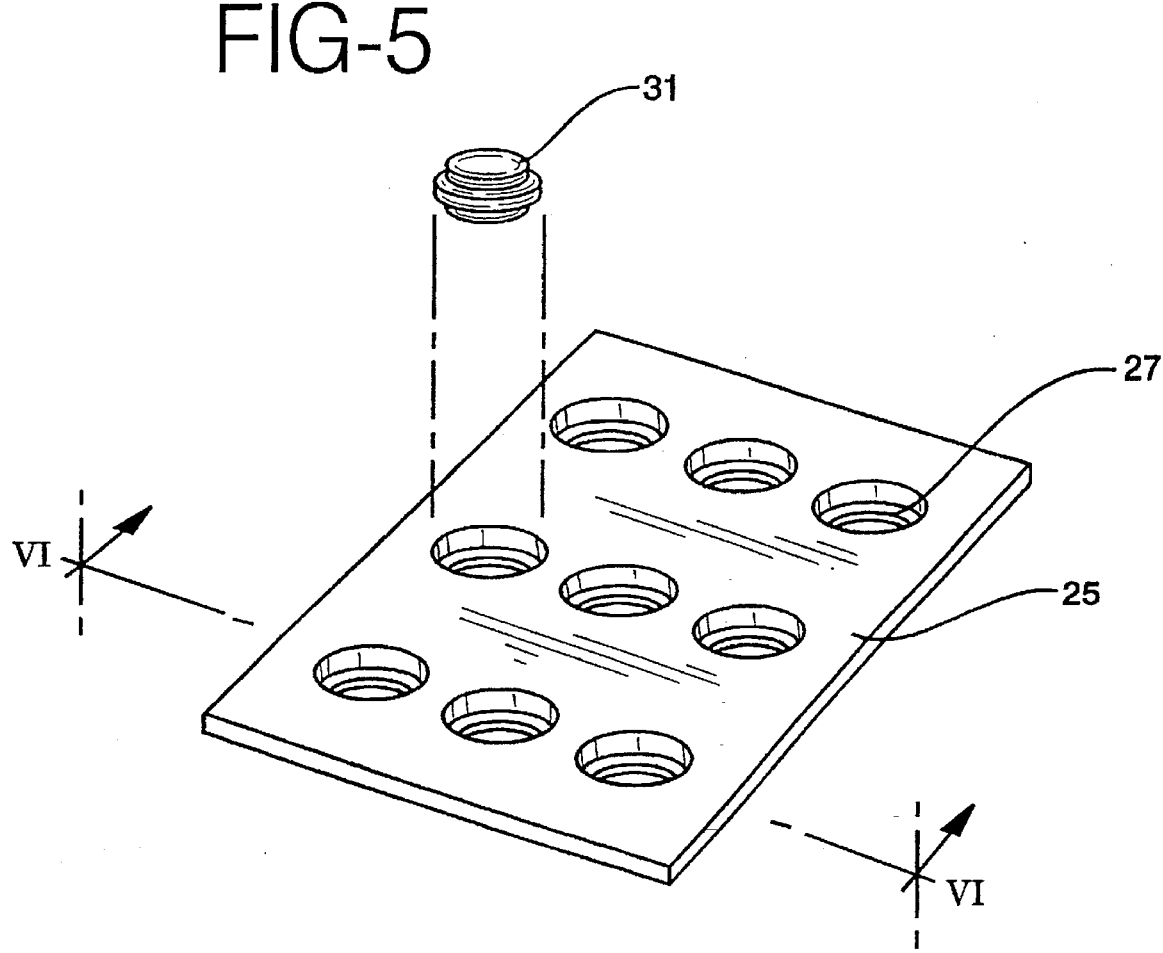
FIG. 5 is a perspective showing of a product package including a formed tablet removed therefrom.
Figure 6:
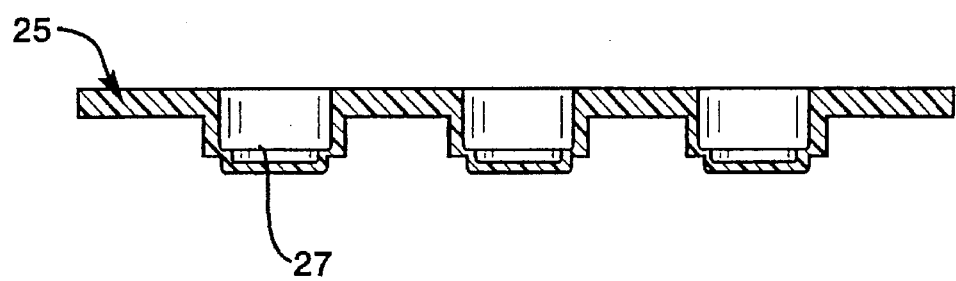
FIG. 6 is a cross-section of the product package of FIG. 5 taken through the lines VI—VI thereof.

Referring now to FIG. 4, a further embodiment of the tableting apparatus of the present invention is shown. Tableting apparatus 60 is a form, fill and seal machine designed for in-line operation in full production. Tableting apparatus 60 forms a tablet package from plastic sheeting, compresses a tablet from tableting feedstock, fills the package with formed tablet and seals the product package in a single continuous operation. Apparatus 60 is a computer controlled automated assembly apparatus which includes an elongate lower cabinet 62 having an upper longitudinal table 64 extending between ends 64a and 64b. Table 64 is linearly movable under the operation of electromechanical drive mechanism (not shown) operated by one or more controllers. A roll of blister or cavity forming plastic sheeting 66 such as plastic sheeting or aluminum/plastic foil laminate is fed into cabinet 62 where cavities 27 are formed in the planar sheeting. The cabinet 62 may contain a heating element and forming dies, preferably a vacuum form die (not shown) for the formation of the multi-cavity product tray 25. Continuously joined product trays 25 of the type shown in FIGS. 5 and 6, are positioned on table 64 for linear movement therealong. While not shown herein table 64 may include thereon appropriately shaped support members such as those described above for supporting and positionally confining product trays 25 for the formation of tablets therein.

Apparatus 60 includes a first station 70 adjacent end 64a of table 64. First station 70 defines a fill station for filling cavities 27 of product tray 25 with tableting feedstock 30. At first station 70 apparatus 60 includes a dispensing assembly 72 which includes an operable support apparatus 73 controlled by controller 74, a feedstock reservoir 76, and an array 78 of dossiters 80 movably supported over table 64 by arm assembly 82.

Dossiter 80 of array 78 may be individual dossiters of the type shown and described with respect to FIG. 2A, arranged in a pattern or array 78 which matches the pattern of cavities 27 of product tray 25. Array 78 is both vertically movable in the direction of arrow B and transversely movable in the direction of arrow C to collect and dispense tableting feedstock 30. Arm assembly 82, operable under controlled operation of support apparatus 73, moves array 78 to reservoir 76 wherein a premeasured amount of tableting feedstock 30 is accumulated in each dossiter 80. As above described, reservoir 76 may be a constant level reservoir which permits a premeasured amount of feedstock 30 to be accumulated in dossiter 80. As also described above, preferably a tablet preform may be formed within each dossiter 80 which may be transferred to a product tray 25 for finish compression into a tablet.

Array 78 is then movable to a product tray 25 supported on table 64 so that each dossiter deposits the premeasured volume of tableting feedstock 30 (or preform) into one of cavity 27 thereof. While not shown herein, a filling block of the type described above, or a similar device may be used to assist in filling each cavity 27 especially where loose feedstock is deposited rather than a tablet preform. After filling, the array is retracted and is moved back to reservoir 76 to start the next cycle for filling the next successive product tray 25, which is linerally indexed to first station 70 by movement of table 64.

In a preferred embodiment, the tablets may be formed directly in the product tray 25 using dossiters 80 or in a manner described above with respect to FIGS. 2A–2D. As mentioned above, it is also contemplated that the dossiters 80 may be used only to deposit feedstock (or tablet preform) into cavities 27 and a separate forming die may be used to form tablets within the product tray.

The product tray 25 having each cavity 27 filled with a premeasured amount of tableting feedstock 30 is moved along table 64 to a second station 84 for formation of tablets 31 therein. Second station 84 includes an overhead support apparatus 83 which is controlled by controller 85 to operably move an array 86 of dies 87 supported by arm 88.

Dies 87 of array 86 may be of the type shown and described above with respect to FIGS. 3A–3C. Dies 87 are arranged in a pattern or array similar to that of array 78 of dossiter 80, which matches the pattern of cavities 27 of product tray 25. Array 86 is vertically movable over table 64 so as to be insertable into and retractable from the cavities 27 of product tray 25. The distance traversed by array 86 and the compacting force applied may be computer controlled so as to provide sufficient force to form tablets 31 in product tray 25. Array 86 is lowered so that dies 87 are inserted in unison into each cavity 27 of tray 25 thereby forming tablets 31. The array 86 is retracted leaving formed tablets 31 therein.

The filled product trays are then linerally indexed along table 64 where upon the next successive filled tray is moved to second station 84 for tablet formation.

The filled product tray 25 is moved from second station 84 to a third station 90 where additional processing steps may be accomplished. For example at location 90 electronic inspection of the filled product trays 25 may take place. Such inspection would include assuring that each cavity is filled with a tablet 31 and that the tablets 31 are the correct size and weight.

After inspection has taken place the product tray 25 may be moved to a fourth station 92 where further secondary operations may take place to yield a suitable packaged product. Operations such as curing the tablets by heat, steam, moisture or other means, placing a sealing lid over product tray 25, die cutting the product tray and sealing lid, labeling the tablet or package (such as by ink jet printing, pad printing, gravure printing or other printing techniques) and boxing the package may occur at this fourth station 92.

Thus, while there have been described what are presently believed to be preferred embodiments of the present invention, those skilled in the art will realize that other and further modifications and changes can be made without departing from the true spirit of the invention, and it is intended to include all such further changes and modifications as come within the scope of the invention.

What is claimed is:

1. A tablet forming method comprising the steps of:
    providing a tablet package having an open ended cavity generally in the shape of said dosage tablet;
    dispensing a premeasured volume of tableting feedstock into said cavity; and
    compacting said premeasured volume of tableting feedstock into a removable low density compression dosage tablet within said cavity.

2. A method of claim 1 wherein said providing steps includes providing a blister package having at least one said cavity.

3. A method of claim 1 wherein said dispensing step includes:
    providing a reservoir containing said tableting feedstock; and
    inserting a dossiter into said reservoir to collect said premeasured volume of tableting feedstock.

4. A method of claim 3 wherein said dispensing step includes:
    placing said dossiter over said cavity; and
    ejecting said premeasured volume of tableting feedstock from said dossiter into said cavity.

5. A method of claim 4 wherein said dossiter includes an open end in communication with a feedstock accumulation chamber and wherein said placing step includes placing said open end of said dossiter into said cavity.

6. A method of claim 5 wherein said dossiter includes a die movably supported within said accumulation chamber and wherein said compacting step includes moving said die into said cavity to compact said feedstock into said tablet.

7. A method of claim 1 wherein said compacting step includes inserting a die having a die portion generally in the shape of said dosage tablet into said cavity.

8. A method of claim 7 further including the step of supporting said tablet package with a support member.

9. A method of claim 8 wherein said support member is of a shape generally similar to the shape of said package.

10. A tablet-forming apparatus comprising:

a packaging support for accommodating a tablet package, said package having a planar surface and at least one tablet cavity therein;

a feedstock dispensing member operably movable with respect to said package support for dispensing tableting feedstock into said cavity; and feedstock compacting means operably movable with respect to said packaging support for compacting said tableting feedstock into a removable low density compression dosage tablet with said cavity.

11. An apparatus of claim 10 further including a feedstock reservoir for accommodating said tableting feedstock, said dispensing member being operably movable between said reservoir and said packaging support for transferring a premeasured volume of feedstock from said reservoir to said package cavity.

12. An apparatus of claim 11 further including a movable table, said table supporting said packaging support and being movable to move said packaging support from a first location adjacent said feedstock dispensing member to a second location adjacent said compacting means.

13. An apparatus of claim 12 wherein said table defines a third location permitting insertion and removal of said package from said packaging support.

14. An apparatus of claim 13 wherein said table is a turntable which is rotatably moveable among said first, second and third locations.

15. An apparatus of claim 12 wherein said table is elongate having a table surface which is movable in a linerally continuous fashion, said table surface being movable to move said packaging support from said first location to said second location.

16. An apparatus of claim 12 further including a third location, said packaging support being movable from said second location to said third location.

17. An apparatus of claim 16 further including packaging sealing means adjacent said third location for sealably covering said cavity of said package.

18. An apparatus of claim 11 wherein said packaging support includes a support base having a plurality of recesses therein, said base being positioned on said table for supporting said tableting package having a plurality of said tablet cavities, each said cavity for residence within one recess of said base.

19. An apparatus of claim 18 wherein said feedstock dispensing member includes a dispenser array, said array having a plurality of discrete feedstock dispensers for transferring in unison feedstock from said reservoir to each of said cavities of said tableting package.

20. An apparatus of claim 19 wherein feedstock compacting means further includes a compacting assembly, said compacting assembly including:

a plurality of elongate rod-like dies; and a support block positionable over said tablet cavities, said support block defining channels which insertably accommodate therein said dies.

21. An apparatus of claim 20 wherein each said rod-like die includes an end thereof insertable into one of said channels of said support block and into said tablet cavity and each said end having a shape generally conforming to the shape of said tablet.

22. An assembly for the formation of compression dosage tablets comprising:

a product package including a generally planar tray having a plurality of cavities therein, each cavity having a shape of one of said tablets;

a support table for supporting said product package, said table being movable so as to move said supported package between at least two positions;

a feedstock dispensing apparatus positioned at one of said two positions for dispensing a premeasured amount of tableting feedstock into said cavities; and a feedstock compacting apparatus positioned at a second one of said two positions for compacting said feedstock dispensed into each said cavity into a tablet therein.

23. An assembly of claim 22 wherein said support table includes a package support member, said package support member includes a planar surface and a plurality of recesses therein, said recesses each accommodating a cavity of said package to positionally confine said package.

24. An assembly of claim 23 wherein said package support member includes a filling block positionable over said product tray, said filling block including plural channels alignable with said cavities of said product tray.

25. An assembly of claim 22 wherein said feedstock dispensing apparatus includes a dossiter for accumulating and dispensing a premeasured amount of feedstock into each of said cavities.

26. An assembly of claim 25 wherein said feedstock dispensing apparatus includes a reservoir containing tableting feedstock, said dossiter being operably movable between said reservoir and said support member for filling each said cavity of said product tray with said premeasured amount of tableting feedstock from said reservoir.

27. An assembly of claim 26 wherein said feedstock dispensing apparatus includes an array of said dossiter, said array being movable between said reservoir and said support member for filling each said container of said product tray in unison.

28. An assembly of claim 27 wherein said feedstock compacting apparatus includes a die insertable into said cavity of said product tray for compacting said feedstock and forming said tablet therein.

29. An assembly of claim 28 wherein said feedstock compacting apparatus includes an array of said dies, said array being insertable into said cavities of said product tray in unison for forming said tablets therein.

30. A method of forming a low density compression dosage tablet comprising the steps of:

providing a feedstock dossiter having a generally cylindrical open ended accumulation chamber and a piston-like die movably supported within said chamber;

collecting a preselected volume of tableting feedstock within said accumulation chamber;

inserting said open end of said accumulation chamber into an open ended cavity of a tablet package; and moving said piston-like die toward said open end of said accumulation chamber to compact said feedstock into said tablet within said package cavity.

31. A method of claim 30 wherein said collecting step further includes:

providing a feedstock reservoir;

inserting said accumulation chamber into said reservoir; and moving said piston-like die away from said open end of said accumulation chamber to effect collection of said feedstock therein.

* * * * *